(12) United States Patent
Nowlan et al.

(10) Patent No.: US 8,663,564 B2
(45) Date of Patent: Mar. 4, 2014

(54) SEQUESTRATION OF CARBON DIOXIDE USING METAL OXIDES

(75) Inventors: Daniel Thomas Nowlan, Hugo, MN (US); Clayton V. McNeff, Andover, MN (US)

(73) Assignee: Sartec Corporation, Anoka, MN (US)

( * ) Notice: Subject to any disclaimer, the term of this patent is extended or adjusted under 35 U.S.C. 154(b) by 184 days.

(21) Appl. No.: 13/113,481

(22) Filed: May 23, 2011

(65) Prior Publication Data

US 2011/0288309 A1 Nov. 24, 2011

Related U.S. Application Data

(60) Provisional application No. 61/347,274, filed on May 21, 2010.

(51) Int. Cl.

| | |
|---|---|
| B01J 21/06 | (2006.01) |
| B01J 27/053 | (2006.01) |
| B01J 27/16 | (2006.01) |
| B01J 19/00 | (2006.01) |
| C07C 69/96 | (2006.01) |
| C07C 68/04 | (2006.01) |
| C07D 317/38 | (2006.01) |

(52) U.S. Cl.
USPC ............ 422/129; 549/230; 558/276; 558/277

(58) Field of Classification Search
None
See application file for complete search history.

(56) References Cited

U.S. PATENT DOCUMENTS

| | | |
|---|---|---|
| 4,138,336 A | 2/1979 | Mendel et al. |
| 5,108,597 A | 4/1992 | Funkenbusch et al. |
| 5,182,016 A | 1/1993 | Funkenbusch et al. |
| 5,264,262 A | 11/1993 | Igararashi |
| 5,271,833 A | 12/1993 | Funkenbusch et al. |
| 5,346,619 A | 9/1994 | Funkenbusch et al. |
| 5,540,834 A | 7/1996 | Carr et al. |
| 2011/0014526 A1* | 1/2011 | Gur .............................. 429/405 |

OTHER PUBLICATIONS

Sakakura, T et al., "Metal-ctalyzed Dimethyl Carbonate Synthesis from Carbon Dioxide and Acetals", J. Org. Chem., vol. 64 1999 , 4506-4508.

Robichaud, Michael J. et al., "An Improved Oil Emulsion Synthesis Method for Large, Porous Zirconia Particles for Packed- or Fluidized-Bed Protein Chromatography", Separation Science and Technology 1997 , 32(15), pp. 2547-2559.

Annen, M. J. et al., "Development of Porous Zirconia Spheres by Polymerization-Induced Colloid Aggregation—Effect of Polymerization Rate", Journal of Material Science 1994 , 29: 6123-6130.

Hou, Zhenshan et al., "Synthesis of dimethyl carbonate using CO2 and methanol: enhancing the conversion by controlling the phase behavior", Green Chemistry, Sep. 4, 2002 , 467-471.

* cited by examiner

*Primary Examiner* — Sun Jae Loewe

(74) *Attorney, Agent, or Firm* — Pauly, Devries Smith & Deffner, L.L.C.

(57) ABSTRACT

Embodiments of the present invention relate to carbon dioxide sequestration systems and methods. In an embodiment, the invention includes a method of sequestering carbon dioxide. The method can include mixing carbon dioxide with an alcohol to form a reaction mixture and contacting the reaction mixture with a metal oxide catalyst under reaction conditions sufficient to produce a carbonate as a reaction product. In an embodiment, the invention includes a carbon dioxide sequestration system. The system can include a carbon dioxide supply source, an alcohol supply source, and a reaction vessel. A metal oxide catalyst can be disposed within the reaction vessel. The system can be configured to mix carbon dioxide from the carbon dioxide supply source with an alcohol from the alcohol supply source to form a reaction mixture and contact the reaction mixture with the metal oxide catalyst. Other embodiments are also described herein.

16 Claims, 13 Drawing Sheets

Calibration graph for the CO₂ pump rate.

GC-MS from reaction of methanol and $CO_2$ over bare $ZrO_2$. The methanol peak has been removed by setting the mass cutoff to 35 – 500 amu.

Proposed mechanism for $CO_2$ sequestration to form dialkyl carbonates catalyzed by bare $ZrO_2$.

6a) Decomposition of 1% DEC over bare $ZrO_2$ at T=200 °C with increasing contact time. 6b) Conversion of $CO_2$ to DEC using bare $ZrO_2$ at T=200 °C versus catalyst contact time.

FIGS. 6A-B

The effect of pressure on the sequestration of $CO_2$ with ethanol to produce DEC using bare $ZrO_2$ at T=200 °C, EtOH = 3.00 mL/min, $CO_2$ = 2.00 mL/min, 1.6 min contact time.

Sequestration of $CO_2$ using bare $ZrO_2$.

| Sample | MeOH (mL/min) | $CO_2$ (mL/min) | $CO_2$ (g/min) | Preheater Temp (°C) | Inlet Temp (°C) | Outlet Temp (°C) | Contact time (min) | Reactor Number | Pressure (PSI) | DMC Conc (mg/g) | % Conv |
|---|---|---|---|---|---|---|---|---|---|---|---|
| ST35-57 Fr1 | 1.5 | 1.5 | 0.491 | 175 | 178 | 175 | 2.7 | 1 | 3400 | 8.86 | 1.05 |
| ST35-57 Fr2 | 2.0 | 2.0 | 0.688 | 175 | 179 | 175 | 2.0 | 1 | 3400 | 7.54 | 0.85 |
| ST35-57 Fr3 | 3.0 | 2.0 | 0.688 | 174 | 181 | 175 | 1.6 | 1 | 3400 | 5.22 | 0.88 |
| ST35-57 Fr4 | 1.5 | 2.0 | 0.305 | 175 | 180 | 175 | 3.2 | 1 | 3400 | 7.38 | 1.40 |
| ST35-57 Fr5 | 1.5 | 1.0 | 0.305 | 200 | 205 | 201 | 3.2 | 1 | 3400 | 8.43 | 1.60 |
| ST35-57 Fr6 | 3.0 | 2.0 | 0.688 | 199 | 208 | 201 | 1.6 | 1 | 3400 | 10.27 | 1.73 |
| ST35-57 Fr7 | 2.0 | 2.0 | 0.688 | 201 | 207 | 200 | 2.0 | 1 | 3400 | 10.62 | 1.19 |
| ST35-57 Fr8 | 1.5 | 1.5 | 0.491 | 199 | 206 | 200 | 2.7 | 1 | 3400 | 11.90 | 1.41 |
| ST35-57 Fr9 | 1.5 | 1.5 | 0.491 | 224 | 232 | 225 | 2.7 | 1 | 3400 | 9.94 | 1.17 |
| ST35-57 Fr10 | 2.0 | 2.0 | 0.688 | 224 | 232 | 225 | 2.0 | 1 | 3400 | 12.21 | 1.37 |
| ST35-57 Fr11 | 3.0 | 2.0 | 0.688 | 224 | 233 | 225 | 1.6 | 1 | 3400 | 7.36 | 1.24 |
| ST35-57 Fr12 | 1.5 | 1.0 | 0.305 | 224 | 231 | 225 | 3.2 | 1 | 3400 | 8.33 | 1.58 |
| ST35-57 Fr13 | 1.5 | 1.0 | 0.305 | 250 | 258 | 251 | 3.2 | 1 | 3400 | 8.12 | 1.54 |
| ST35-57 Fr14 | 1.5 | 1.5 | 0.491 | 249 | 257 | 250 | 2.7 | 1 | 3400 | 10.53 | 1.24 |
| ST35-57 Fr15 | 2.0 | 2.0 | 0.688 | 249 | 258 | 250 | 2.0 | 1 | 3400 | 13.28 | 1.49 |
| ST35-57 Fr16 | 3.0 | 2.0 | 0.688 | 250 | 258 | 250 | 1.6 | 1 | 3400 | 10.24 | 1.73 |
| ST35-57 Fr17 | 10.0 | 1.0 | 0.305 | 250 | 256 | 252 | 0.7 | 1 | 3400 | 7.50 | 9.50 |

FIG. 8

Sequestration of $CO_2$ using phosphoric acid modified $ZrO_2$.

| Sample | MeOH (mL/min) | $CO_2$ (mL/min) | $CO_2$ (g/min) | Preheater Temp (°C) | Inlet Temp (°C) | Outlet Temp (°C) | Contact time (min) | Reactor Number | Pressure (PSI) | DMC Conc (mg/g) | % Conv |
|---|---|---|---|---|---|---|---|---|---|---|---|
| ST35-58Fr1 | 1.5 | 1.5 | 0.491 | 175 | 174 | 174 | 2.7 | 2 | 3400 | 0.54 | 0.06 |
| ST35-58Fr2 | 1.5 | 1.0 | 0.305 | 175 | 176 | 175 | 3.2 | 2 | 3400 | 0.09 | 0.01 |
| ST35-58Fr3 | 2.0 | 2.0 | 0.688 | 174 | 178 | 175 | 2.0 | 2 | 3400 | 0.10 | 0.01 |
| ST35-58Fr4 | 3.0 | 2.0 | 0.688 | 175 | 178 | 175 | 1.6 | 2 | 3400 | 0.09 | 0.01 |
| ST35-58Fr5 | 1.5 | 1.0 | 0.305 | 200 | 202 | 200 | 3.2 | 2 | 3400 | 0.34 | 0.07 |
| ST35-58Fr6 | 1.5 | 1.5 | 0.491 | 200 | 202 | 200 | 2.7 | 2 | 3400 | 0.37 | 0.04 |
| ST35-58Fr7 | 2.0 | 2.0 | 0.688 | 200 | 204 | 200 | 2.0 | 2 | 3400 | 0.17 | 0.02 |
| ST35-58Fr8 | 3.0 | 2.0 | 0.688 | 200 | 204 | 200 | 1.6 | 2 | 3400 | 0.18 | 0.03 |
| ST35-58Fr9 | 1.5 | 1.0 | 0.305 | 224 | 227 | 225 | 3.2 | 2 | 3400 | 0.18 | 0.03 |
| ST35-58Fr10 | 1.5 | 1.5 | 0.491 | 224 | 228 | 225 | 2.7 | 2 | 3400 | 0.84 | 0.10 |
| ST35-58Fr11 | 2.0 | 2.0 | 0.688 | 225 | 229 | 225 | 2.0 | 2 | 3400 | 1.99 | 0.22 |
| ST35-58Fr12 | 3.0 | 2.0 | 0.688 | 225 | 230 | 225 | 1.6 | 2 | 3400 | 1.56 | 0.26 |
| ST35-58Fr13 | 1.5 | 1.0 | 0.305 | 249 | 253 | 250 | 3.2 | 2 | 3400 | 1.40 | 0.27 |
| ST35-58Fr14 | 1.5 | 1.5 | 0.491 | 250 | 254 | 250 | 2.7 | 2 | 3400 | 2.00 | 0.24 |
| ST35-58Fr15 | 2.0 | 2.0 | 0.688 | 250 | 255 | 250 | 2.0 | 2 | 3400 | 1.86 | 0.21 |
| ST35-58Fr16 | 3.0 | 2.0 | 0.688 | 248 | 256 | 250 | 1.6 | 2 | 3400 | 1.40 | 0.24 |
| ST35-58Fr17 | 10.0 | 1.0 | 0.305 | 248 | 252 | 250 | 0.7 | 2 | 3400 | 0.25 | 0.32 |

FIG. 9

Sequestration of $CO_2$ using sulfuric acid modified $ZrO_2$.

| Sample | MeOH (mL/min) | $CO_2$ (mL/min) | $CO_2$ (g/min) | Preheater Temp (°C) | Inlet Temp (°C) | Outlet Temp (°C) | Contact time (min) | Catalyst | Pressure (PSI) | DMC Conc (mg/g) | % Conv |
|---|---|---|---|---|---|---|---|---|---|---|---|
| ST35-59Fr1 | 1.5 | 1.0 | 0.305 | 175 | 192 | 175 | 3.2 | 3 | 3400 | 0.18 | 0.03 |
| ST35-59Fr2 | 1.5 | 1.5 | 0.491 | 175 | 190 | 175 | 2.7 | 3 | 3400 | 0.41 | 0.05 |
| ST35-59Fr3 | 2.0 | 2.0 | 0.688 | 175 | 190 | 175 | 2.0 | 3 | 3400 | 0.42 | 0.05 |
| ST35-59Fr4 | 3.0 | 2.0 | 0.688 | 175 | 190 | 175 | 1.6 | 3 | 3400 | 0.13 | 0.02 |
| ST35-59Fr5 | 1.5 | 1.0 | 0.305 | 200 | 218 | 201 | 3.2 | 3 | 3400 | 0.07 | 0.01 |
| ST35-59Fr6 | 1.5 | 1.5 | 0.491 | 200 | 216 | 200 | 2.7 | 3 | 3400 | 0.83 | 0.10 |
| ST35-59Fr7 | 2.0 | 2.0 | 0.688 | 200 | 216 | 200 | 2.0 | 3 | 3400 | 1.05 | 0.12 |
| ST35-59Fr8 | 3.0 | 2.0 | 0.688 | 200 | 217 | 200 | 1.6 | 3 | 3400 | 0.97 | 0.16 |
| ST35-59Fr9 | 1.5 | 1.0 | 0.305 | 225 | 242 | 225 | 3.2 | 3 | 3400 | 0.06 | 0.01 |
| ST35-59Fr10 | 1.5 | 1.5 | 0.491 | 224 | 242 | 225 | 2.7 | 3 | 3400 | 0.43 | 0.05 |
| ST35-59Fr11 | 2.0 | 2.0 | 0.688 | 224 | 242 | 225 | 2.0 | 3 | 3400 | 0.59 | 0.07 |
| ST35-59Fr12 | 3.0 | 2.0 | 0.688 | 225 | 243 | 225 | 1.6 | 3 | 3400 | 0.21 | 0.04 |
| ST35-59Fr13 | 1.5 | 1.0 | 0.305 | 250 | 265 | 248 | 3.2 | 3 | 3400 | 0.07 | 0.01 |
| ST35-59Fr14 | 1.5 | 1.5 | 0.491 | 250 | 267 | 250 | 2.7 | 3 | 3400 | 0.09 | 0.01 |
| ST35-59Fr15 | 2.0 | 2.0 | 0.688 | 249 | 268 | 250 | 2.0 | 3 | 3400 | 0.11 | 0.01 |
| ST35-59Fr16 | 3.0 | 2.0 | 0.688 | 248 | 269 | 249 | 1.6 | 3 | 3400 | 0.13 | 0.02 |
| ST35-59Fr17 | 10.0 | 2.0 | 0.688 | 248 | 263 | 249 | 0.7 | 3 | 3400 | 0.40 | 0.22 |
| ST35-59Fr18 | 10.0 | 1.0 | 0.305 | 250 | 264 | 250 | 0.7 | 3 | 3400 | 0.07 | 0.01 |

FIG. 10

Sequestration of $CO_2$ using ethanol and bare $ZrO_2$.

| Sample | EtOH (mL/min) | $CO_2$ (mL/min) | $CO_2$ (g/min) | Preheater Temp (°C) | Inlet Temp (°C) | Outlet Temp (°C) | Contact time (min) | Reactpr Number | Pressure (PSI) | DEC Conc (mg/g) | % Conv |
|---|---|---|---|---|---|---|---|---|---|---|---|
| ST35-43 Fr1 | 3.00 | 2.00 | 0.688 | 200 | 199 | 188 | 1.6 | 4 | 3500 | 5.15 | 0.66 |
| ST35-43 Fr2 | 2.00 | 3.00 | 1.031 | 200 | 200 | 200 | 1.6 | 4 | 3500 | 2.84 | 0.22 |
| ST35-43 Fr3 | 4.00 | 1.00 | 0.305 | 200 | 200 | 200 | 1.6 | 4 | 3500 | 1.54 | 0.60 |
| ST35-43 Fr4 | 1.00 | 4.00 | 1.398 | 200 | 200 | 200 | 1.6 | 4 | 3500 | 2.51 | 0.20 |
| ST35-42 Fr1 | 3.00 | 2.00 | 0.688 | 226 | 219 | 225 | 1.6 | 4 | 3500 | 2.07 | 0.27 |
| ST35-42 Fr2 | 2.00 | 3.00 | 1.031 | 224 | 219 | 225 | 1.6 | 4 | 3500 | 1.58 | 0.12 |
| ST35-44 Fr1 | 3.00 | 2.00 | 0.688 | 248 | 236 | 250 | 1.6 | 4 | 3500 | 1.17 | 0.15 |
| ST35-44 Fr2 | 2.00 | 3.00 | 1.031 | 250 | 234 | 250 | 1.6 | 4 | 3500 | 0.97 | 0.08 |
| ST35-44 Fr3 | 4.00 | 1.00 | 0.305 | 251 | 237 | 249 | 1.6 | 4 | 3500 | 0.59 | 0.23 |
| ST35-44 Fr4 | 1.00 | 4.00 | 1.398 | 250 | 233 | 250 | 1.6 | 4 | 3500 | 0.79 | 0.06 |

FIG. 11

Production data for the sequestration of $CO_2$ by other alcohols. Abbreviations: n-PrOH = n-propanol, EG = Ethylene Glycol, n-BuOH = n-butanol, i-PrOH = isopropyl alcohol, DPC = dipropyl carbonate, EC = Ethylene carbonate, DBC = dibutyl carbonate, DIPC = diisopropyl carbonate.

| Sample | Alcohol | ROH (mL/min) | $CO_2$ (mL/min) | $CO_2$ (g/min) | Preheater Temp (°C) | Inlet Temp (°C) | Outlet Temp (°C) | Contact time (min) | Reactor Number | Pressure (PSI) | Product Carbonate Observed |
|---|---|---|---|---|---|---|---|---|---|---|---|
| ST35-54 Fr1 | n-PrOH | 2.00 | 1.00 | 0.305 | 200 | 207 | 200 | 2.7 | 4 | 3400 | DPC, Yes |
| ST35-54 Fr2 | n-PrOH | 3.00 | 2.00 | 0.688 | 200 | 206 | 200 | 1.6 | 4 | 3400 | DPC, Yes |
| ST35-54 Fr3 | EG | 3.00 | 2.00 | 0.688 | 201 | 208 | 200 | 1.6 | 4 | 3400 | EC, Yes |
| ST35-54 Fr4 | EG | 2.00 | 1.00 | 0.305 | 200 | 207 | 200 | 2.7 | 4 | 3400 | EC, Yes |
| ST35-54 Fr5 | n-BuOH | 3.00 | 2.00 | 0.688 | 200 | 207 | 200 | 1.6 | 4 | 3400 | DBC, Yes |
| ST35-54 Fr6 | n-BuOH | 2.00 | 1.00 | 0.305 | 200 | 206 | 200 | 2.7 | 4 | 3400 | DBC, Yes |
| ST35-54 Fr7 | i-PrOH | 3.00 | 2.00 | 0.688 | 201 | 207 | 200 | 1.6 | 4 | 3400 | DIPC, Yes |
| ST35-54 Fr8 | i-PrOH | 2.00 | 1.00 | 0.305 | 201 | 207 | 199 | 2.7 | 4 | 3400 | DIPC, Yes |

FIG. 12

Optimized conditions for the production of dimethyl carbonate from $CO_2$ and methanol using bare zirconia as the catalyst in a continuous flow reactor.

| Sample | MeOH (mL/min) | CO2 (mL/min) | CO2 (g/min) | Preheater Temp (oC) | Inlet Temp (oC) | Outlet Temp (oC) | Contact time (min) | Reactor Number | Pressure (PSI) | DMC Conc (mg/g) | % Conv |
|---|---|---|---|---|---|---|---|---|---|---|---|
| ST35-61Fr1 | 2.0 | 2.0 | 0.688 | 249 | 258 | 250 | 2.0 | 1 | 3400 | 13.28 | 1.5 |
| ST35-61Fr2 | 3.0 | 2.0 | 0.688 | 250 | 258 | 250 | 1.6 | 1 | 3400 | 10.24 | 1.7 |
| ST35-61Fr3 | 10.0 | 2.0 | 0.688 | 248 | 252 | 250 | 0.67 | 1 | 3500 | 5.43 | 3.1 |
| ST35-61Fr4 | 12.0 | 2.0 | 0.688 | 250 | 252 | 250 | 0.57 | 1 | 3500 | 6.81 | 4.6 |

FIG. 13

SEQUESTRATION OF CARBON DIOXIDE USING METAL OXIDES

This application claims the benefit of U.S. Provisional Application No. 61/347,274, filed May 21, 2010, the content of which is herein incorporated by reference in its entirety.

FIELD OF THE INVENTION

The present invention relates to carbon dioxide sequestration systems and methods. More specifically, the present invention relates to carbon dioxide sequestration systems with metal oxide catalysts and related methods.

BACKGROUND OF THE INVENTION

The global carbon cycle is heavily influenced by the activities of humans. For example, the combustion of fuels by human is believed to have resulted in a large increase in the amount of carbon dioxide present in the atmosphere. In the last hundred years, global fossil carbon emissions have increased by more than a factor of ten. As nations around the globe continue to become more industrialized, demands for energy are expected to increase dramatically. As such, in the absence of new technological solutions, it is believed that the trend toward increased fossil carbon emissions will continue.

Carbon dioxide is considered to be a "greenhouse" gas and is believed to have contributed to global warming trends. Carbon dioxide, along with water vapor, methane, nitrous oxide, and ozone, causes more heat to be retained by the Earth than would otherwise be captured. The global average air temperature near the Earth's surface rose 0.74±0.18° C. during the last 100 years. It is believed that this is due, at least in part, to the observed increase in greenhouse gas concentrations. Further increases in global temperatures may lead to various catastrophic effects including a rising sea level, increased extreme weather events, reduced agricultural yields, glacier retreat, and species extinction, amongst others.

In an effort to prevent catastrophic events from occurring, significant resources have been devoted to developing systems to reduce the amount of carbon dioxide emitted into the atmosphere. However, many existing systems have various issues relating to cost, throughput, robustness, and the like.

SUMMARY OF THE INVENTION

Embodiments of the present invention relate to carbon dioxide sequestration systems and methods. In an embodiment, the invention includes a method of sequestering carbon dioxide. The method can include mixing carbon dioxide with an alkyl alcohol to form a reaction mixture and contacting the reaction mixture with a metal oxide catalyst under reaction conditions sufficient to produce a carbonate as a reaction product.

In an embodiment, the invention includes a carbon dioxide sequestration system. The system can include a carbon dioxide supply source, an alcohol supply source, and a reaction vessel. A metal oxide catalyst can be disposed within the reaction vessel. The system can be configured to mix carbon dioxide from the carbon dioxide supply source with an alkyl alcohol from the alcohol supply source to form a reaction mixture and contact the reaction mixture with the metal oxide catalyst.

The above summary of the present invention is not intended to describe each discussed embodiment of the present invention. This is the purpose of the figures and the detailed description that follows.

BRIEF DESCRIPTION OF THE FIGURES

The invention may be more completely understood in connection with the following drawings, in which:

FIG. 8 is a table showing details of sequestration of $CO_2$ using bare (unmodified) $ZrO_2$.

FIG. 9 is a table showing details of sequestration of $CO_2$ using phosphoric acid modified $ZrO_2$.

FIG. 10 is a table showing details of sequestration of $CO_2$ using sulfuric acid modified $ZrO_2$.

FIG. 11 is a table showing details of sequestration of $CO_2$ using ethanol and bare (unmodified) $ZrO_2$.

FIG. 12 is a table showing details of sequestration of $CO_2$ using various alcohols.

FIG. 13 is a table showing details of the production of dimethyl carbonate from $CO_2$ and methanol using bare zirconia in a continuous flow reactor.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

Applicants have discovered that carbon dioxide can be usefully sequestered through a reaction with an alcohol in the presence of a metal oxide catalyst. By way of example, carbon dioxide can be reacted with an alkyl alcohol in order to create reaction products such as carbonates. An example of the reaction is shown below in equation 1, wherein the alkyl alcohol is ethanol and the carbonate is diethylcarbonate (DEC).

$$2CH_3CH_2OH + CO_2 \leftrightarrow DEC + H_2O \quad (1)$$

As such, in an embodiment herein, the invention includes a method of sequestering carbon dioxide including mixing carbon dioxide with an alkyl alcohol to form a reaction mixture and contacting the reaction mixture with a metal oxide catalyst under reaction conditions sufficient to produce a carbonate as a reaction product.

The carbonate reaction products are relatively high value materials because they are useful in many applications. For example, diethyl carbonate has been investigated as an oxygenated diesel fuel additive and has potential over MTBE due to its immiscibility in water and low potential for environmental toxicity. This approach to forming diethyl carbonate eliminates the need for carbon monoxide, a highly toxic gas, and replaces it with carbon dioxide.

While not intending to be bound by theory, it is believed that embodiments of sequestration systems and methods included herein can offer various advantages. For example, the metal oxides used as catalysts herein (described in greater detail below) have extreme stability under various temperature and pressure conditions making them well-suited to processing steps under extreme conditions. In addition, such metal oxide catalysts can be reused many times, making them very cost effective. Various aspects of exemplary embodiments will now be described in greater detail.

Reaction Systems

Figure 1:
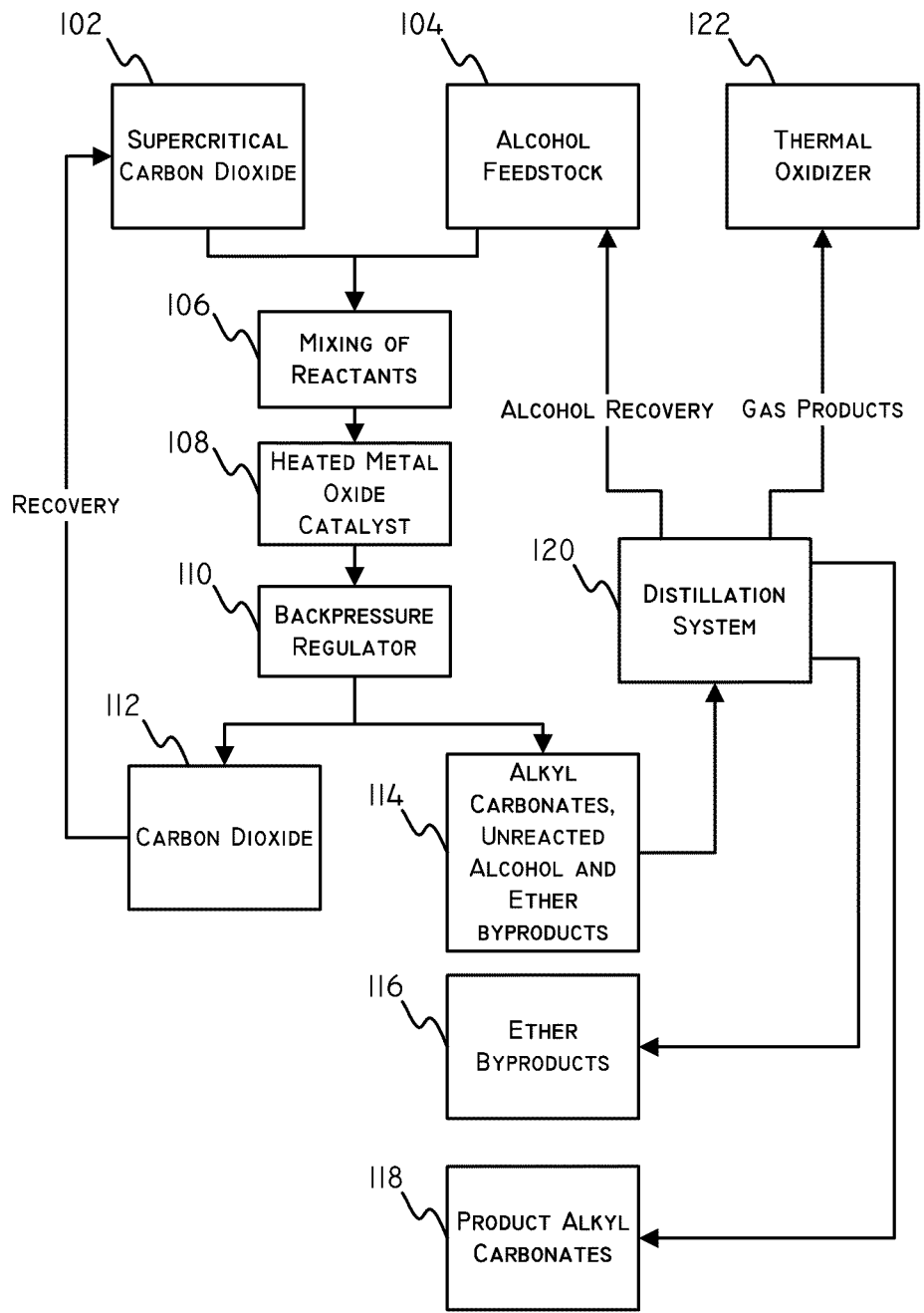
FIG. 1 is a schematic diagram of a carbon dioxide sequestration system in accordance with an embodiment.

Referring now to FIG. 1, a schematic diagram of an exemplary carbon dioxide sequestration system is shown in accordance with an embodiment. A carbon dioxide feedstock can be provided from a carbon dioxide supply source 102. In some embodiments, the carbon dioxide can be supplied under supercritical conditions. An alcohol feedstock can be provided from an alcohol supply source 104.

In a first operation 106, the carbon dioxide and the alcohol can be mixed. In a second operation 108, the mixed reactants can be contacted with a metal oxide catalyst. The reaction conditions can be as described below. In a third operation 110, the product mixture can pass through a back-pressure regulator. Residual carbon dioxide 112 can then be returned to the carbon dioxide supply source 102.

The rest of the product mixture 114, including alkyl carbonates, unreacted alcohol, and ether byproducts, can then pass to a distillation system 120. The distillation system 120 can separate out various components of the reaction mixture. Specifically, the distillation system 120 can separate out the ether byproducts 116 and the produced alkyl carbonates 118. The distillation system 120 can also separate out residual alcohol which can be returned to the alcohol supply source 104. Finally, remaining gaseous products can pass to a thermal oxidizer 122. While FIG. 1 is an example of a sequestration apparatus, it will be appreciated that various changes can be made to the apparatus while still remaining within the scope herein.

Metal Oxide Catalysts

Metal oxide catalysts used with embodiments of the invention can include metal oxides with surfaces including Lewis acid sites, Bronsted base sites, and Bronsted acid sites. By definition, a Lewis acid is an electron pair acceptor. A Bronsted base is a proton acceptor and a Bronsted acid is a proton donor. Metal oxide catalysts of the invention can specifically include zirconia, alumina, titania and hafnia. Metal oxide catalysts of the invention can also include silica clad with a metal oxide selected from the group consisting of zirconia, alumina, titania, hafnia, zinc oxide, copper oxide, magnesium oxide and iron oxide. In some embodiments, the metal oxide catalyst can be of a single metal oxide type. By way of example, in some embodiments, the metal oxide catalyst is substantially pure titania. In some embodiments, the metal oxide catalyst is substantially pure alumina. Metal oxide catalysts of the invention can also include mixtures of metal oxides, such as mixtures of metal oxides including zirconia, alumina, titania and/or hafnia. Of the various metal oxides that can be used with embodiments of the invention, zirconia, titania, alumina and hafnia are advantageous as they are very chemically and thermally stable and can withstand very high temperatures and pressures as well as extremes in pH. Titania and alumina are advantageous because of the additional reason that they are less expensive materials.

Metal oxides of the invention can include metal oxide particles clad with carbon. Carbon clad metal oxide particles can be made using various techniques such as the procedures described in U.S. Pat. Nos. 5,108,597; 5,254,262; 5,346,619; 5,271,833; and 5,182,016, the contents of which are herein incorporated by reference. Carbon cladding on metal oxide particles can render the surface of the particles more hydrophobic.

Metal oxides of the invention can also include polymer coated metal oxides. By way of example, metal oxides of the invention can include a metal oxide coated with polybutadiene (PBD). Polymer coated metal oxide particles can be made using various techniques such as the procedure described in Example 1 of U.S. Pub. Pat. App. No. 2005/0118409, the contents of which are herein incorporated by reference. Polymer coatings on metal oxide particles can render the surface of the particles more hydrophobic.

Metal oxide catalysts of the invention can be made in various ways. As one example, a colloidal dispersion of zirconium dioxide can be spray dried to produce aggregated zirconium dioxide particles. Colloidal dispersions of zirconium dioxide are commercially available from Nyacol Nano Technologies, Inc., Ashland, Mass. The average diameter of particles produced using a spray drying technique can be varied by changing the spray drying conditions. Examples of spray drying techniques are described in U.S. Pat. No. 4,138,336 and U.S. Pat. No. 5,108,597, the contents of both of which are herein incorporated by reference. It will be appreciated that other methods can also be used to create metal oxide particles. One example is an oil emulsion technique as described in Robichaud et al., Technical Note, "An Improved Oil Emulsion Synthesis Method for Large, Porous Zirconia Particles for Packed- or Fluidized-Bed Protein Chromatography," Sep. Sci. Technol. 32, 2547-59 (1997). A second example is the formation of metal oxide particles by polymer induced colloidal aggregation as described in M. J. Annen, R. Kizhappali, P. W. Carr, and A. McCormick, "Development of Porous Zirconia Spheres by Polymerization-Induced Colloid Aggregation-Effect of Polymerization Rate," J. Mater. Sci. 29, 6123-30 (1994). A polymer induced colloidal aggregation technique is also described in U.S. Pat. No. 5,540,834, the contents of which are herein incorporated by reference.

Metal oxide catalysts used in embodiments of the invention can be sintered by heating them in a furnace or other heating device at a relatively high temperature. In some embodiments, the metal oxide is sintered at a temperature of about 160° C. or greater. In some embodiments, the metal oxide is sintered at a temperature of about 400° C. or greater. In some embodiments, the metal oxide is sintered at a temperature of about 600° C. or greater. Sintering can be done for various amounts of time depending on the desired effect. Sintering can make metal oxide catalysts more durable. In some embodiments, the metal oxide is sintered for more than about 30 minutes. In some embodiments, the metal oxide is sintered for more than about 3 hours. However, sintering also reduces the surface area. In some embodiments, the metal oxide is sintered for less than about 1 week.

In some embodiments, the metal oxide catalyst is in the form of particles. Particles within a desired size range can be specifically selected for use as a catalyst. For example, particles can be sorted by size using techniques such as air classification, elutriation, settling fractionation, or mechanical screening. In some embodiments, the size of the particles is greater than about 0.2 µm. In some embodiments, the size range selected is from about 0.2 µm to about 1 mm. In some embodiments, the size range selected is from about 0.2 µm to about 400 µm. In some embodiments, the size range selected is from about 1 µm to about 100 µm. In some embodiments, the size range selected is from about 5 µm to about 15 µm. In some embodiments, the average size selected is about 10 µm. In some embodiments, the average size selected is about 5 µm.

In some embodiments, metal oxide particles used with embodiments of the invention are porous. By way of example, in some embodiments the metal oxide particles can have an average pore size of about 30 angstroms to about 2000 angstroms. However, in other embodiments, metal oxide particles used are non-porous.

The physical properties of a porous metal oxide can be quantitatively described in various ways such as by surface area, pore volume, porosity, and pore diameter. In some embodiments, metal oxide catalysts of the invention can have a surface area of between about 1 and about 200 m²/gram. Pore volume refers to the proportion of the total volume taken up by pores in a material per weight amount of the material. In some embodiments, metal oxide catalysts of the invention can have a pore volume of between about 0.01 mL/g and about 2 mL/g. Porosity refers to the proportion within a total volume that is taken up by pores. As such, if the total volume of a particle is 1 cm³ and it has a porosity of 0.5, then the volume taken up by pores within the total volume is 0.5 cm³. In some embodiments, metal oxide catalysts of the invention can have a porosity of between about 0 and about 0.8. In some embodiments, metal oxide catalysts of the invention can have a porosity of between about 0.3 and 0.6.

Metal oxide particles used with embodiments of the invention can have various shapes. By way of example, in some embodiments the metal oxide can be in the form of spherules. In other embodiments, the metal oxide can be a monolith. In some embodiments, the metal oxide can have an irregular shape.

The Lewis acid sites on metal oxides of the invention can interact with Lewis basic compounds. Thus, Lewis basic compounds can be bonded to the surface of metal oxides of the invention. A Lewis base is an electron pair donor. Lewis basic compounds of the invention can include anions formed from the dissociation of acids such as hydrobromic acid, hydrochloric acid, hydroiodic acid, nitric acid, sulfuric acid, perchloric acid, boric acid, chloric acid, phosphoric acid, pyrophosphoric acid, chromic acid, permanganic acid, phytic acid and ethylenediamine tetramethyl phosphonic acid (EDTPA), and the like. Lewis basic compounds of the invention can also include hydroxide ion as formed from the dissociation of bases such as sodium hydroxide, potassium hydroxide, lithium hydroxide and the like.

The anion of an acid can be bonded to a metal oxide of the invention by refluxing the metal oxide in an acid solution. By way of example, metal oxide particles can be refluxed in a solution of sulfuric acid. Alternatively, the anion formed from dissociation of a base, such as the hydroxide ion formed from dissociation of sodium hydroxide, can be bonded to a metal oxide by refluxing in a base solution. By way of example, metal oxide particles can be refluxed in a solution of sodium hydroxide. The base or acid modification can be achieved under exposure to the acid or base in either batch or continuous flow conditions when disposed in a reactor housing at elevated temperature and pressure to speed up the adsorption/modification process. In some embodiments, fluoride ion, such as formed by the dissociation of sodium fluoride, can be bonded to the particles.

In some embodiments, metal oxide particles can be packed into a housing, such as a column. Disposing metal oxide particles in a housing is one approach to facilitating continuous flow processes. Many different techniques may be used for packing the metal oxide particles into a housing. The specific technique used may depend on factors such as the average particle size, the type of housing used, etc. Generally speaking, particles with an average size of about 1-20 microns can be packed under pressure and particles with an average size larger than 20 microns can be packed by dry-packing/tapping methods or by low pressure slurry packing. In some embodiments, the metal oxide particles of the invention can be impregnated into a membrane, such as a PTFE membrane.

However, in some embodiments, metal oxide catalysts used with embodiments of the invention are not in particulate form. For example, a layer of a metal oxide can be disposed on a substrate in order to form a catalyst used with embodiments of the invention. The substrate can be a surface that is configured to contact the alcohol feedstock during processing. In one approach, a metal oxide catalyst can be disposed as a layer over a surface of a reactor that contacts the alcohol feedstock. Alternatively, the metal oxide catalyst can be embedded as a particulate in the surface of an element that is configured to contact the alcohol feedstock during processing.

Reaction Conditions

In some embodiments, the reaction temperature is about 150° Celsius or higher. In some embodiments, the reaction temperature is about 200° Celsius or higher. In some embodiments, the reaction temperature is about 250° Celsius or higher. In some embodiments, the reaction temperature is about 300° Celsius or higher. In some embodiments, the reaction temperature is from about 100° Celsius to about 400° Celsius. In some embodiments, the reaction temperature is from about 150° Celsius to about 250° Celsius.

The reaction mixture may be passed over the metal oxide catalyst for a length of time sufficient for the reaction to reach a desired level of completion. This will, in turn, depend on various factors including the temperature of the reaction, the chemical nature of the catalyst, the surface area of the catalyst, the contact time with the catalyst and the like. In an embodiment, the contact time is between about 0.1 seconds and 2 hours. In an embodiment, the contact time is between about 1 second and 20 minutes. In an embodiment, the contact time is between about 2 seconds and 1 minute.

In some embodiments, the reaction mixture is kept under pressure during the reaction in order to prevent components of the reaction mixture (such as the co-reactant feedstock) from vaporizing. The reactor housing can be configured to withstand the pressure under which the reaction mixture is kept. In addition, a backpressure regulator can be used to maintain a desired pressure. A desirable pressure for the reactor can be estimated with the aid of the Clausius-Clapeyron equation. Specifically, the Clausius-Clapeyron equation can be used to estimate the vapor pressures of a liquid. The Clausius-Clapeyron equation is as follows:

$$\ln\left(\frac{P_1}{P_2}\right) = \frac{\Delta H_{vap}}{R}\left(\frac{1}{T_2} - \frac{1}{T_1}\right)$$

wherein $\Delta H_{vap}$=is the enthalpy of vaporization; $P_1$ is the vapor pressure of a liquid at temperature $T_1$; $P_2$ is the vapor pressure of a liquid at temperature $T_2$, and R is the ideal gas constant.

In an embodiment, the pressure inside the housing is greater than the vapor pressures of any of the components of the reaction mixture. In an embodiment, the pressure is greater than about 500 psi. In an embodiment, the pressure is greater than about 800 psi. In an embodiment, the pressure is greater than about 1000 psi. In an embodiment, the pressure is greater than about 1500 psi. In an embodiment, the pressure is greater than about 2000 psi. In an embodiment, the pressure is greater than about 3000 psi. In an embodiment, the pressure is greater than about 3000 psi. In an embodiment, the pressure is greater than about 4000 psi. In an embodiment, the pressure is greater than about 5000 psi.

While not intending to be bound by theory, it is believed that pressure can impact conversion rates and/or totals of the sequestration reaction. Pressures that are insufficiently low can result in non-optimal conversion. Pressures that are too high can also result in non-optimal conversion. In some embodiments, the pressure can be from about 1000 PSI to about 5000 PSI. In some embodiments, the pressure can be from about 2500 PSI to about 4500 PSI. In some embodiments, the pressure can be from about 3000 PSI to about 4000 PSI. In some embodiments, the pressure can be from about 3250 PSI to about 3750 PSI.

In some embodiments, the temperature and pressure conditions for the reaction can be a supercritical temperature and pressure for the reactants. By way of example, in some embodiments the temperature and pressure can be supercritical for carbon dioxide. In some embodiments, the temperature and pressure can be supercritical for the alcohol. In some embodiments, the temperature and pressure can be supercritical for both carbon dioxide and the alcohol.

Alcohols

Embodiments of the invention can sequester carbon dioxide though a reaction with an alcohol as catalyzed by a metal oxide catalyst. Exemplary alcohols can include aliphatic, aromatic, and alicyclic alcohols. In some embodiments, alcohols can include C1-C30 alcohols (alcohols with one to thirty carbon atoms). In some embodiments, alcohols can include C1-C6 alkyl alcohols. Alcohols used herein can be monofunctional or multi-functional (e.g., one alcohol moiety or multiple alcohol moieties). Exemplary alcohols can specifically include methanol, ethanol, propanol, isopropyl alcohol, butanol, and the like. In a particular embodiment the alcohol is ethanol.

Alcohols used with embodiments herein can include those formed through fermentation processes. By way of example, biomass can be fermented by microorganisms in order to produced alcohol feedstocks. Virtually any living organism is a potential source of biomass for use in fermentation processes. As such, alcohol feedstocks can be derived from industrial processing wastes, food processing wastes, mill wastes, municipal/urban wastes, forestry products and forestry wastes, agricultural products and agricultural wastes, amongst other sources.

Though not limiting the scope of possible sources, specific examples of biomass crop sources for alcohol production can include corn, poplar, switchgrass, reed canary grass, willow, silver maple, black locust, sycamore, sweetgum, sorghum, miscanthus, eucalyptus, hemp, maize, wheat, soybeans, alfalfa, and prairie grasses.

$CO_2$ Sources

Carbon dioxide, for use in carbon dioxide sequestration systems as described herein can be obtained in various ways. In some embodiments, carbon dioxide can be extracted from ambient air. Dry air generally includes about 380 parts per million of carbon dioxide. Carbon dioxide can be extracted from air through various processes including molecular sieve systems or cooling systems that cause carbon dioxide to freeze, thereby facilitating separation.

In some embodiments, carbon dioxide can be obtained as a waste product from other industrial processes. By way of example, fermentation processes generate a substantial amount of carbon dioxide as a waste product. As another example, the combustion of hydrocarbons, such as coal, oil, and natural gas, generates a substantial amount of carbon dioxide. Effluent streams of waste materials, such as waste gases, can be captured from these industrial processes and then processed using carbon dioxide sequestration systems as described herein. In some embodiments, gases from such industrial processes can simply be directed into a carbon dioxide sequestration system. In some embodiments, systems included herein can include devices such as molecular sieves, cryogenic purification systems, or other devices to extract out and thereby concentrate carbon dioxide before sequestration in operations such as shown herein.

The present invention may be better understood with reference to the following examples. These examples are intended to be representative of specific embodiments of the invention, and are not intended as limiting the scope of the invention.

EXAMPLES

Example 1

Formation of Microspheres 2000 grams of porous zirconia microspheres were synthesized by spray drying of colloidal zirconia followed by air classification to obtain 10 micron catalyst microspheres. The data for these particles are shown in Table 1.

TABLE 1

10 µm $ZrO_2$ properties.

| | |
|---|---|
| Surface Area (m2/g) | 22.2 |
| Pore volumne (mL/g) | 0.13 |
| Pore diameter (angstrom) | 240 |
| Internal Porosity | 0.43 |
| Average size range (micron) | 5-15 |
| Size Standard Deviation (um) | 2.78 |
| D90/D10 (Size Distribution) | 1.84 |

Phosphoric acid modified zirconia microspheres (10 micron size) were prepared by adding unmodified porous zirconia (100 g) to 500 mL of 1.5 molar phosphoric acid in a 1000 mL round bottom flask. The microsphere suspension was sonicated under vacuum for approximately 10 minutes while swirling to degas and fully suspend the microspheres. The flask was then attached to a water-cooled condenser and heating mantle and the solution refluxed continuously for 6 hours. The heat source was removed and the flask was allowed to cool to room temperature. The suspension was filtered on a medium frit sintered glass funnel, and then rinsed thoroughly with four 200 mL aliquots of HPLC-grade water followed by three 100 mL acetone rinses. Air was pulled through the particle cake for 8 hours until the particles were dry and free flowing.

Sulfuric acid modified zirconia microspheres (10 micron size) were prepared by adding unmodified porous zirconia (100 g) to 500 mL of 1.5 molar sulfuric acid in a 1000 mL round bottom flask. The microsphere suspension was sonicated under vacuum for approximately 10 minutes while swirling to degas and fully suspend the microspheres. The flask was then attached to a water-cooled condenser and heating mantle and the solution refluxed continuously for 6 hours. The heat source was removed and the flask was allowed to cool to room temperature. The suspension was filtered on a medium frit sintered glass funnel, and then rinsed thoroughly with four 200 mL aliquots of HPLC-grade water followed by three 100 mL acetone rinses. Air was pulled through the particle cake for 8 hours until the particles were dry and free flowing.

Example 2

Packing of Columns

Table 2 contains conditions for packing the fixed be reactors used herein. In general, the catalyst microspheres as synthesized above were slurried in ethanol (30 g zirconia in 60 mL of ethanol) and packed into a 10.0 mm (i.d.)×150 mm length stainless steel HPLC tube at 7,000 psi using ethanol as a pusher solvent. The reactor was allowed to pack for 30 minutes under pressure and then the pressure was allowed to slowly bleed off. The end fitting and frit were then attached to the inlet of the column (Reactors 1-4, Table 2). A larger column was packed to investigate longer contact times. This 50 cm×21.2 mm column (Reactor #5, Table 2) was packed with bare zirconia by dry packing methods.

TABLE 2

Packing conditions for reactors (columns) used in herein.

| Reactor Number | Length (cm) | I.D. (mm) | Packing Method | Catalyst | Slurry solvent | Pusher solvent | Pressure (psi) | Time (min) |
|---|---|---|---|---|---|---|---|---|
| 1 | 15 | 10 | Slurry | $ZrO_2$ | EtOH | EtOH | 7000 | 28 |
| 2 | 15 | 10 | Slurry | $PO_4/ZrO_2$ | EtOH | EtOH | 7000 | 30 |
| 3 | 15 | 10 | Slurry | $SO_4/ZrO_2$ | EtOH | EtOH | 7000 | 30 |
| 4 | 15 | 10 | Slurry | $ZrO_2$ | EtOH | EtOH | 7000 | 31 |
| 5 | 50 | 21.2 | Dry | $ZrO_2$ | N/A | N/A | N/A | N/A |

Example 3

Assembly of Reactor Apparatus

Figure 2:
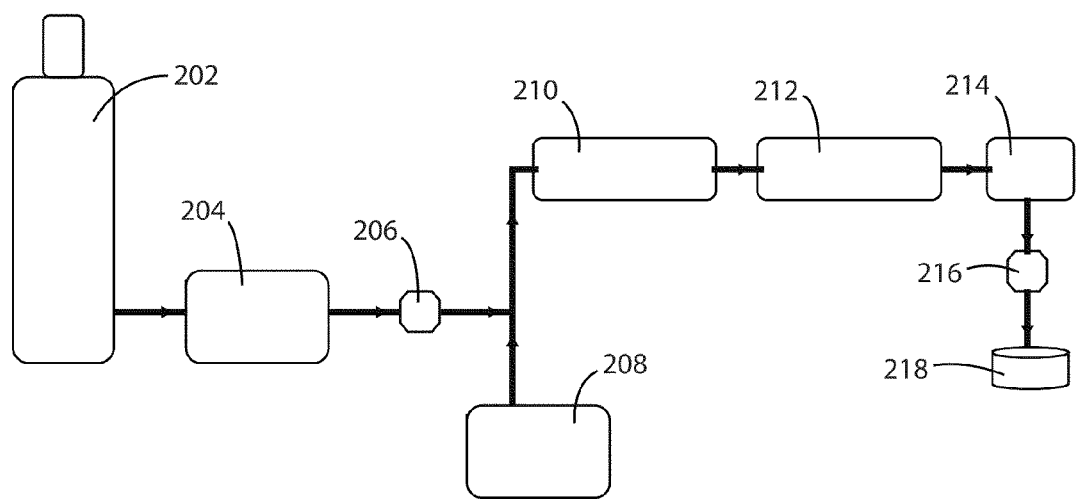
FIG. 2 is a schematic diagram of an embodiment of a reactor apparatus.

The apparatus used herein is shown schematically in FIG. 2. The apparatus consisted of a carbon dioxide tank 202 and a supercritical carbon dioxide pump 204 connected by a T-junction joining it to the alcohol pump 208. However, in order to achieve constant flow rates, a backpressure regulator 206 was placed immediately after the $CO_2$ pump 204 and before the T-junction. The back pressure was set to a value higher than the overall reaction back pressure (e.g. set $CO_2$ BP regulator to 5000 psi when the overall system back pressure for the reaction was set to 3500 psi), the pump was set to pump at a pressure lower than the regulator and the flow rate feature was used to determine the amount of carbon dioxide delivered to the system. In this way, the constant pressure pump was modified to be a constant flow pump. The alcohol (from a supply reservoir not shown) was delivered into the system using a Waters 590 HPLC pump 208. The combined effluent streams were passed through a tube coiled around an 800 W aluminum block preheater 210. The hot effluent was then passed over the hot catalyst particles packed in a stainless steel HPLC column 212 (150 mm×10 mm) that was kept a constant temperature using a column heater. The reaction mixture was cooled by placing the tubing in a water bath 214. Finally, the effluent traveled through a backpressure regulator 216 where the effluent spontaneously separated into an alcoholic phase and gaseous $CO_2$ phase before passing to a product collector 218.

Figure 3:
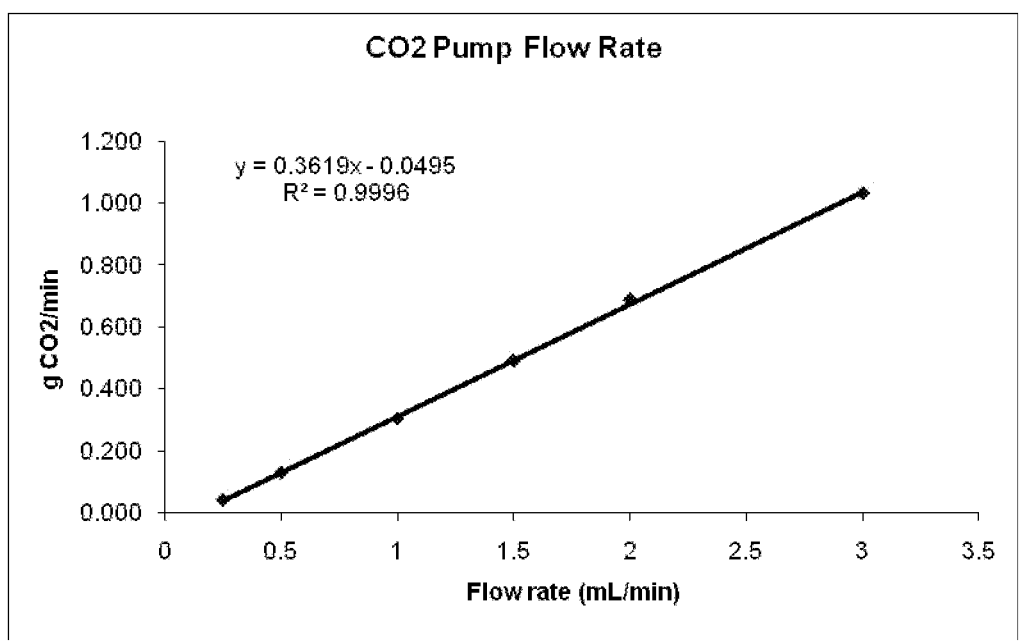
FIG. 3 is a calibration graph of a $CO_2$ pump rate.

The $CO_2$ sequestration system was then subjected to flow rate testing and pressure testing to determine the stability of the system and reproducibility. The flow of alcohol was measured by weighing a collected sample of alcohol for a given amount of time. Multiple flow rates were tested for the alcohol pump to ensure linearity. The amount of $CO_2$ produced per minute at different flow rates was measured by displacement of a known volume of water (using the ideal gas law to calculate the mass of $CO_2$ needed to displace the volume of water). Multiple $CO_2$ flow rates were analyzed and a calibration curve for the $CO_2$ pump was constructed from the data collected (g/min $CO_2$ produced versus $CO_2$ flow rate) shown in FIG. 3. Once the flow rates were determined the ability of the system to operate and remain stable at different pressures and temperatures was examined. It was determined that the system was stable under the reaction conditions that were to be used.

Example 4

Sequestration of $CO_2$ with Bare Unmodified Zirconia Catalyst

The sequestration of $CO_2$ using methanol was systematically investigated at different temperatures, contact times and molar ratios (175-200° C., 0.5-40 min, 2:1-30:1 MeOH: $CO_2$). Selected data are displayed in FIG. 8. The conversion of $CO_2$ to dimethyl carbonate was measured by gas chromatography using FID detection. Standards of DMC in methanol were prepared fresh and used to generate calibration curves for quantitation.

Figure 4:
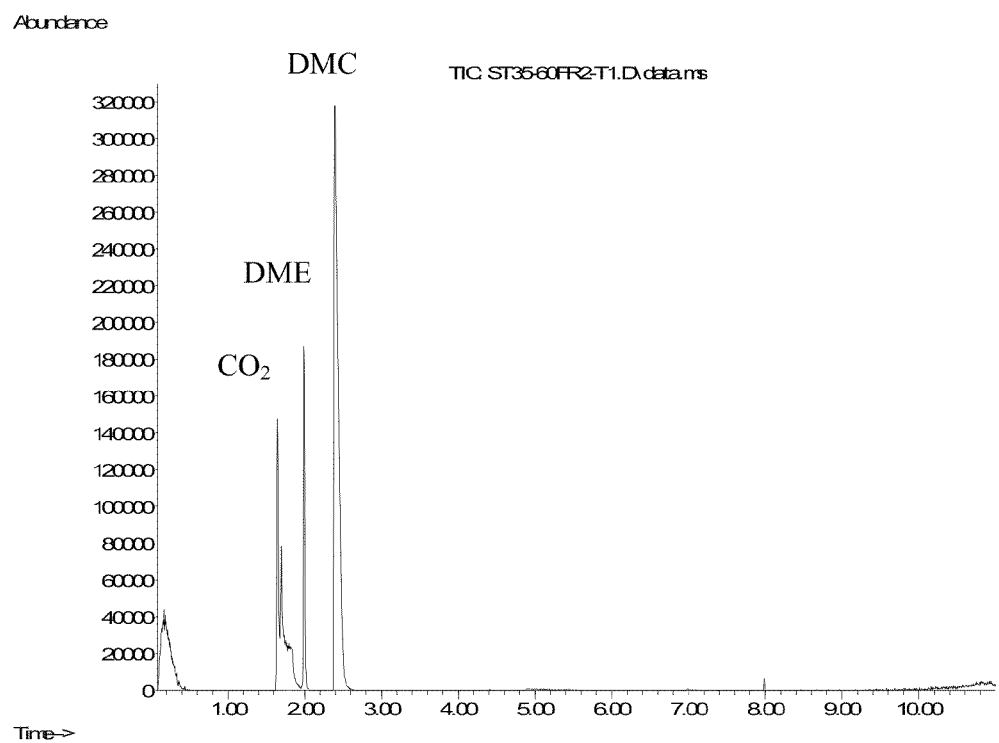
FIG. 4 is a graph showing the results of GC-MS analysis of the reaction of methanol and $CO_2$ over bare (unmodified) $ZrO_2$.

The reaction products were analyzed by GC-MS as well to determine if there were any by-products produced. The methanol peak was excluded from the GC-MS collection by setting the mass detector cutoff to greater than amu values of 35 as shown in a representative chromatogram in FIG. 4. Only $CO_2$, dimethyl ether and dimethyl carbonate were observed in the GC-MS spectra recorded. The $^1$H-NMR spectra for selected samples also revealed only the presence of methanol, dimethyl ether and dimethyl carbonate as the reaction products. GC-FID analysis also contained only methanol, dimethyl ether and dimethyl carbonate as the reaction products under all the conditions investigated.

A gas sample was collected at a set of high yielding conditions (ST35-57 Fraction 15) to determine the amount of dimethyl ether produced during the course of the reaction. The extent of dimethyl ether production in the liquid phase was determined to be 0.4% by GC-FID, and no DME was observed in FTIR for the selected sample. It should be noted that dimethyl ether is a valuable chemical industrially, having use as a propellant and as a refrigerant. The production of DME during the capture of $CO_2$ provides opportunity for extracting another valuable chemical produced during this process.

Example 5

Sequestration of $CO_2$ with Acid Modified Zirconia Catalyst

Reactors (columns) containing phosphoric acid modified zirconia and sulfuric acid modified zirconia were packed and studied under identical conditions to those using bare zirconia (Table 2, Reactors 2 and 3). In this way, the effect of modifying the zirconia could be examined. The conversion of $CO_2$ to dimethyl carbonate was measured by gas chromatography using FID detection. Standards of DMC in methanol were prepared fresh and used to generate calibration curves for quantitation. The results are summarized in FIG. 9 for the phosphoric acid and in FIG. 10 for the sulfuric acid modified zirconia.

Unexpectedly, we observed a decrease in conversion for both phosphoric acid modified zirconia and sulfuric acid modified zirconia. We found that the unmodified zirconia is a superior catalyst. These results are contrary to previously reported increases in catalytic activity for acid modified zirconia. See Ikeda et al., *Promoting effect of phosphoric acid on zirconia catalysts in selective synthesis of dimethyl carbonate from methanol and carbon dioxide.* Cat. Let. 66:59-62. (2000). The product array produced using either of these catalysts is the same as with the unmodified zirconia catalyst, however the amounts of products are different. The decrease in dimethyl carbonate yield is accompanied by an increase in dimethyl ether production. From a mechanistic view, the protonation of methanol is important to the production of dimethyl ether, hence the increase in yield with increase in acidity of the zirconia surface. Again, the dehydration of methanol is well known and has been shown to be very efficient over sulfated zirconia under similar conditions.

Figure 5:
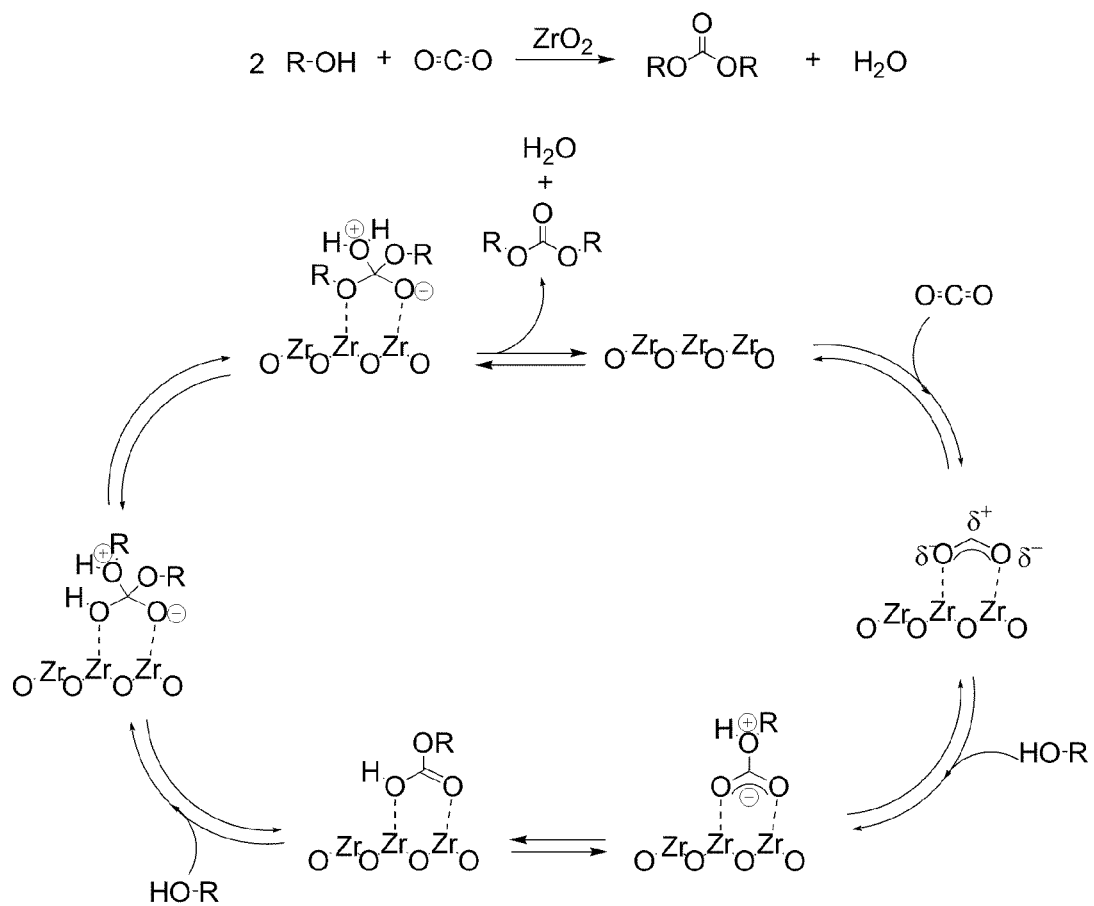
FIG. 5 is a diagram showing a proposed mechanism for $CO_2$ sequestration to form dialkyl carbonates as catalyzed by bare (unmodified) $ZrO_2$.

These observations suggest that the interaction of the $CO_2$ with zirconia surface is pivotal to its activation and subsequent conversion to the product carbonate. If protonation of the carbon dioxide by a surface acid were an important step in the conversion to the carbonate an increase in the overall conversion would be expected for the modified zirconia catalysts. Instead, the lewis acidic nature of the zirconia surface appears to be responsible for activating the $CO_2$ molecule. Once activated, the methanol then undergoes a nucleophilic addition to yield a carbonic acid that can either undergo reversible extrusion of the methanol or further addition of another molecule of methanol followed by water loss to yield the product carbonate. A proposed mechanism for the reaction is shown in FIG. 5.

Example 6

Sequestration of $CO_2$ using Longer Chain Alcohols

The sequestration of $CO_2$ using longer chain alcohols was also investigated. The other alcohols selected for study were ethanol, n-propanol, i-propanol, n-butanol and ethylene glycol. Using the optimal conditions for methanol and $CO_2$ as a starting point (3 mL/min alcohol, 2 mL/min $CO_2$, T=200° C., using bare $ZrO_2$) each of these alcohols was briefly investigated to determine feasibility of conversion to their corresponding carbonates. Special emphasis was given to ethyl alcohol because of the attractive implications for the use of a renewable alcohol in order to sequester $CO_2$. The data support that all of the alcohols used could be converted to their target carbonates.

Example 7

Conversion of Supercritical $CO_2$ to Diethyl Carbonate

The conversion of $CO_2$ to another valuable carbonate was demonstrated by changing the alcohol feedstock from methanol to ethanol. The product diethyl carbonate (DEC) has many appealing qualities. The analysis of the product mixture is much simpler than with methanol as the product carbonate has a significantly higher boiling point than its corresponding alcohol allowing for analysis by GC-MS and an easier separation. From a practical standpoint, ethanol is a renewable resource making its use in the sequestration of $CO_2$ a very attractive concept. The conversion of $CO_2$ to diethyl carbonate was measured by gas chromatography using MS detection. Standards of DEC in ethanol were prepared fresh and used to generate calibration curves for quantitation. The production of DEC from $CO_2$ was investigated at different temperatures, molar ratios of ethanol to carbon dioxide and catalyst contact times. Data for the production of DEC are presented in FIG. 11.

Figure 6:
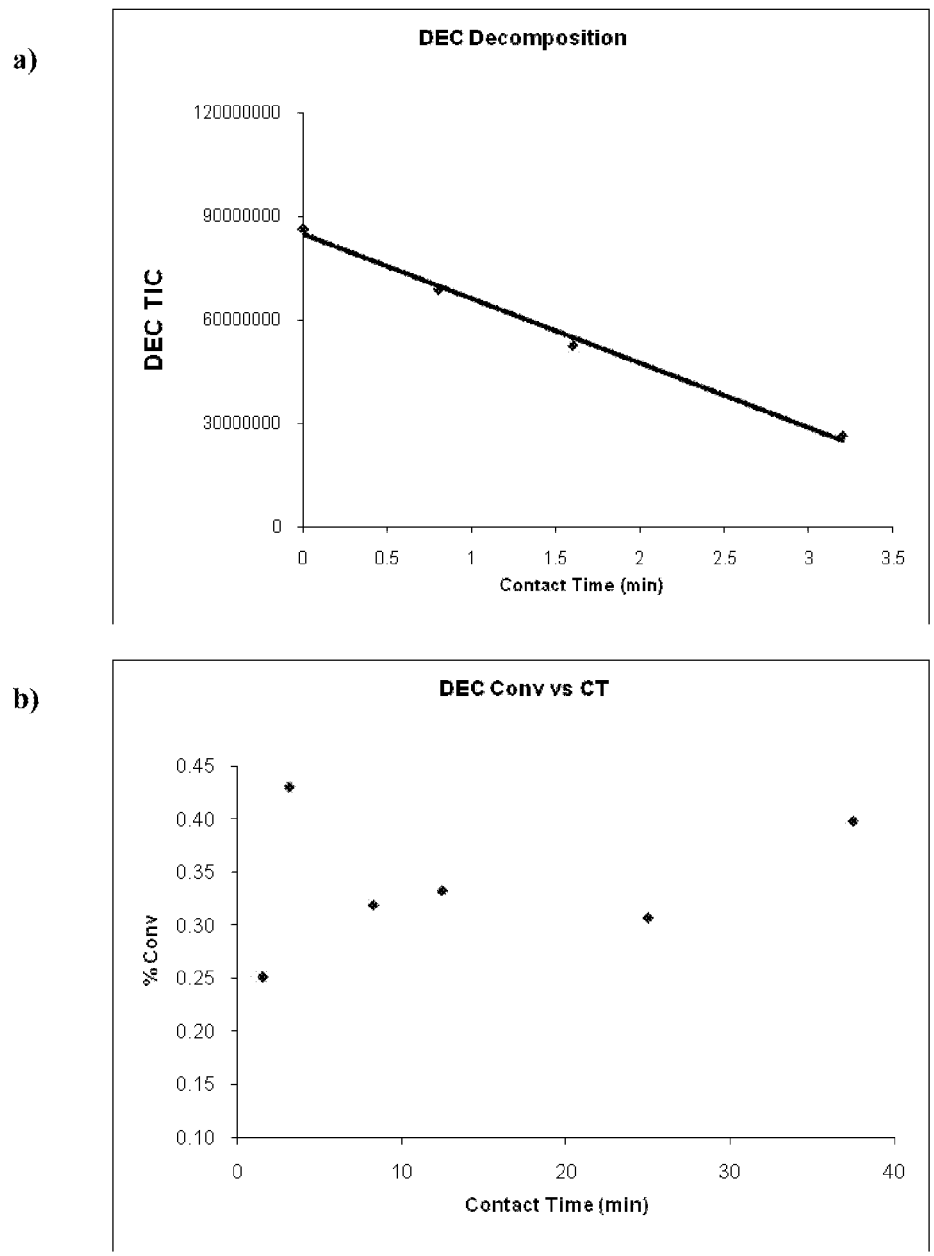
FIG. 6A is a graph showing decomposition of 1% DEC over bare (unmodified) $ZrO_2$ at 200 degrees Celsius with increasing contact time.
FIG. 6B is a graph showing conversion of $CO_2$ to DEC using bare (unmodified) $ZrO_2$ at 200 degrees Celsius versus catalyst contact time.

The best conditions tested for the production of DEC were found to be similar to those for DMC production in terms of alcohol to carbon dioxide ratio, but surprisingly at a lower temperature. The overall yield of DEC was not as high as that of DMC, under the conditions tested herein. As the temperature was increased the yield of DEC decreased. The optimum temperature was found to be 200° C. with diminished yields at 225 and 250° C. This decrease in DEC yield led to the hypothesis that the DEC product may not be stable under the reaction conditions. A catalyst contact time study was undertaken to determine the stability of DEC at the optimal temperature of 200° C. A 1% solution of DEC was prepared and subjected to the reaction conditions at various contact times. The collected fractions were analyzed by GC-MS and the results are presented in FIG. 6a. The DEC concentration decreases in a linear fashion ($R^2$=0.994) with increasing catalyst contact time. A further study was conducted to determine if the DEC is establishing equilibrium at longer contact times. The production of DEC was investigated at 200° C. and long contact times using reactor 5 (Table 2). The data obtained are shown in FIG. 6b. The DEC appears to establish its equilibrium concentration quickly (maximum yield at a 3.2 min contact time at 3000 psi). This implies that the reaction happens very rapidly and is largely unaffected by increases in catalyst contact time. This clearly shows the equilibrium nature of the reaction and the effect of competitive etherification reactions on the yield of the target compound.

Figure 7:
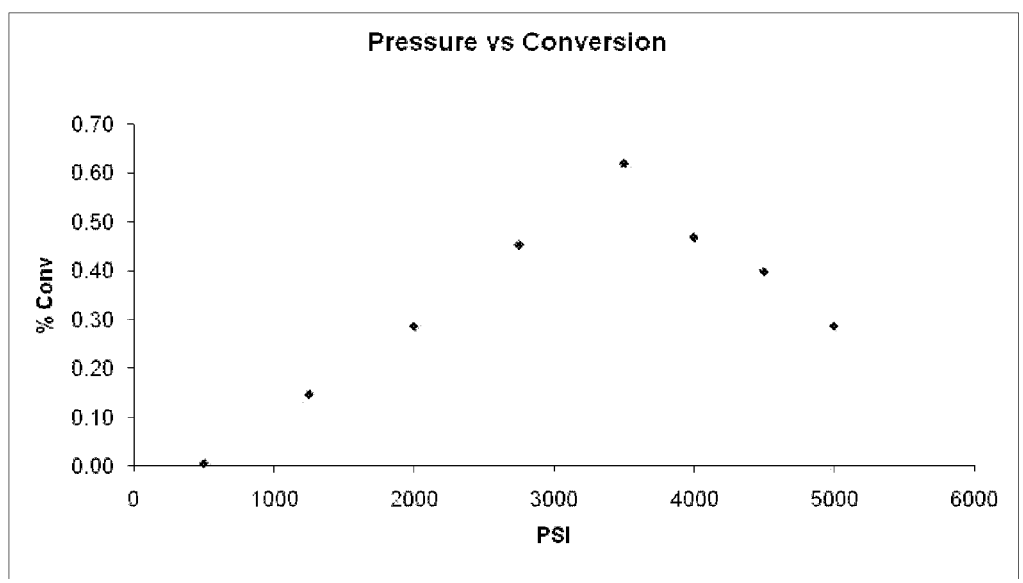
FIG. 7 is a graph showing the effect of pressure on the sequestration of $CO_2$ with ethanol to produce DEC.

Encouraged by those results the effect of pressure on the sequestration of $CO_2$ by ethanol was investigated. The conditions studied were: 3.00 mL/min ethanol, 2.00 mL/min $CO_2$, T=200° C., bare $ZrO_2$, ct=1.6 min. A maximum yield of 0.64% of DEC was observed at 3500 psi and the yield began to decrease at higher or lower pressures. The plot is shown in FIG. 7.

The product array for DEC production was analyzed by GC-MS analysis. The number of products formed is greater than what was observed with methanol. For the optimal conditions the observed products are diethyl ether, diethyl carbonate and diethyl acetaldehyde acetal. As the temperature and contact time with the catalyst are both increased the product array becomes increasingly complex resulting in the formation of a wide array of reaction products but a lower overall DEC yield which translates to a decreased ability to sequester $CO_2$.

Example 8

Conversion of Supercritical $CO_2$ to Higher Carbonates

The sequestration of carbon dioxide using n-propanol, ethylene glycol, i-propanol and n-butanol as the alcohol sources to produce dipropyl carbonate, ethylene carbonate, diisopropyl carbonate and dibutyl carbonate, respectively, was successfully demonstrated. The reaction mixtures were analyzed by GC-MS. The conditions are shown in FIG. 12.

Example 9

Variation of Contact Time and Molar Ratio of Methanol to $CO_2$

In order to optimize the conditions for the formation of dialkyl carbonates we chose to focus on the specific system of dimethyl carbonate by varying the contact time and molar ratio of methanol to $CO_2$ (0.57-2 min, 5:1-18:1). It was hypothesized that increasing the methanol content should lead to increased yields, due to the equilibrium nature of the process. The data obtained from these experiments are shown in FIG. 13. The amount of methanol was subsequently increased while keeping the $CO_2$ flow low (the $CO_2$ pump was displaying poorer performance at lower flow rates during these experiments, so an optimal flow rate of 2 mL/min was selected). This optimization approach resulted in an increase in conversion of the $CO_2$ from a maximum of 1.7% (Table 3) to 4.6%.

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention. As such, it should be understood that many variations and modifications may be made while remaining within the spirit and scope of the invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, device, or other structure that is constructed or configured to perform a particular task or adopt a particular configuration. The phrase "configured" can be used interchangeably with other similar phrases such as arranged and configured, constructed and arranged, constructed, manufactured and arranged, and the like.

The invention claimed is:

1. A method of sequestering carbon dioxide comprising:
   mixing carbon dioxide with an alcohol to form a reaction mixture; and
   contacting the reaction mixture with a metal oxide catalyst under reaction conditions sufficient to produce a carbonate as a reaction product;
   wherein the metal oxide catalyst is selected from the group consisting of alumina, hafnia, titania, and zirconia.

2. The method of claim 1, the metal oxide catalyst comprising an unmodified metal oxide.

3. The method of claim 1, the metal oxide catalyst comprising a particulate.

4. The method of claim 1, the metal oxide catalyst comprising microspheres.

5. The method of claim 1, the metal oxide catalyst comprising an average diameter of between about 0.2 μm to about 400 μm.

6. The method of claim 1, the alcohol comprising an alkyl alcohol.

7. The method of claim 1, the reaction conditions comprising a temperature of greater than about 150 degrees Celsius.

8. The method of claim 1, the reaction conditions comprising a temperature of about 200 degrees Celsius.

9. The method of claim 1, the reaction conditions comprising supercritical conditions for carbon dioxide.

10. The method of claim 1, the reaction conditions comprising a pressure of greater than 1000 PSI.

11. The method of claim 1, the reaction conditions comprising a pressure of less than 5000 PSI.

12. The method of claim 1, the reaction conditions comprising a pressure of between 3000 PSI and 4000 PSI.

13. The method of claim 1, the reaction conditions comprising a pressure of between 3250 PSI and 3750 PSI.

14. The method of claim 1, the carbonate comprising a dialkyl carbonate.

15. The method of claim 1, the carbonate comprising a tetralkyl carbonate.

16. The method of claim 1, wherein contacting the reaction mixture with a metal oxide catalyst under reaction conditions sufficient to produce a carbonate as a reaction product is performed as part of a continuous flow process.

\* \* \* \* \*